United States Patent [19]
Brown

[11] 3,969,006
[45] July 13, 1976

[54] MEDICAL EMERGENCY TREATMENT CABINET

[76] Inventor: Loy G. Brown, 609 Fairchild Drive, Fort Worth, Tex. 76114

[22] Filed: Sept. 13, 1973

[21] Appl. No.: 396,746

[52] U.S. Cl. .............................. 312/234.1; 24/67 R; 312/209; 312/279
[51] Int. Cl.² ...................... A47B 81/00; B42F 1/00
[58] Field of Search ............ 312/209, 234.1–234.5, 312/209, 279; 35/17; 40/78.15; 218/DIG. 3; 24/67 R, 67.11

[56] References Cited
UNITED STATES PATENTS

| | | | |
|---|---|---|---|
| 663,083 | 12/1900 | Kolb | 24/67 R X |
| 745,978 | 12/1903 | Urie et al. | 24/67 R UX |
| 1,353,974 | 9/1920 | Smith | 312/279 X |
| 1,644,830 | 10/1927 | Henderson | 312/209 |
| 1,778,423 | 10/1930 | Kells | 40/78.1 J |
| 1,944,405 | 1/1934 | Copeland | 312/279 X |
| 2,119,609 | 6/1938 | Stiles | 312/234.1 |
| 2,330,276 | 9/1943 | Foster | 248/DIG. 3 |
| 2,682,932 | 7/1954 | Howard | 312/209 X |
| 2,828,928 | 4/1958 | Kollisch | 312/234.1 X |
| 2,860,943 | 11/1958 | Brawner | 312/279 X |
| 2,882,111 | 4/1959 | Sease et al. | 312/279 |
| 3,041,957 | 7/1962 | Liptay | 312/209 X |
| 3,080,203 | 3/1963 | Graham | 312/234.4 |
| 3,085,844 | 4/1963 | Mancini | 312/209 X |
| 3,200,960 | 8/1965 | Banse | 312/234.1 X |
| 3,393,030 | 7/1968 | Block | 312/209 X |
| 3,428,383 | 2/1969 | Nobel | 312/209 |
| 3,775,867 | 12/1973 | Christenberry | 35/17 |

FOREIGN PATENTS OR APPLICATIONS 1,308,489   9/1962   France ............................ 312/234.1

Primary Examiner—Donald A. Griffin
Attorney, Agent, or Firm—Warren H. Kintzinger

[57] ABSTRACT

A medical emergency patient treatment unit that contains a variety of emergency treatment medications, supplies and equipment, all grouped in coordinate end use groups color coded to referenced sets of emergency treatment instructions in a medical treatment book mounted thereon. The treatment units are designed to be readily removed and stationed in locations of probable emergency situation occurrence.

1 Claim, 2 Drawing Figures

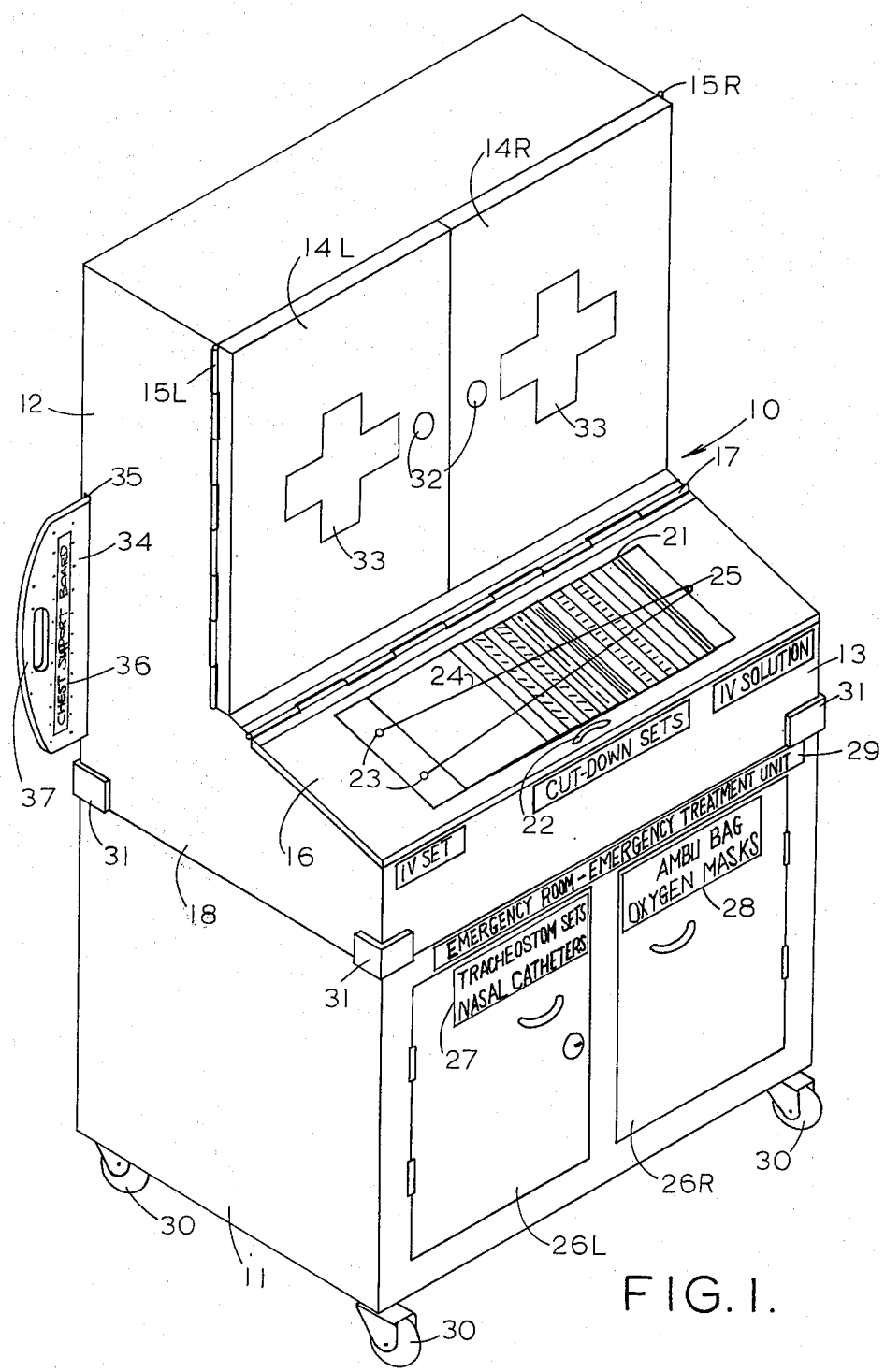
FIG. I.

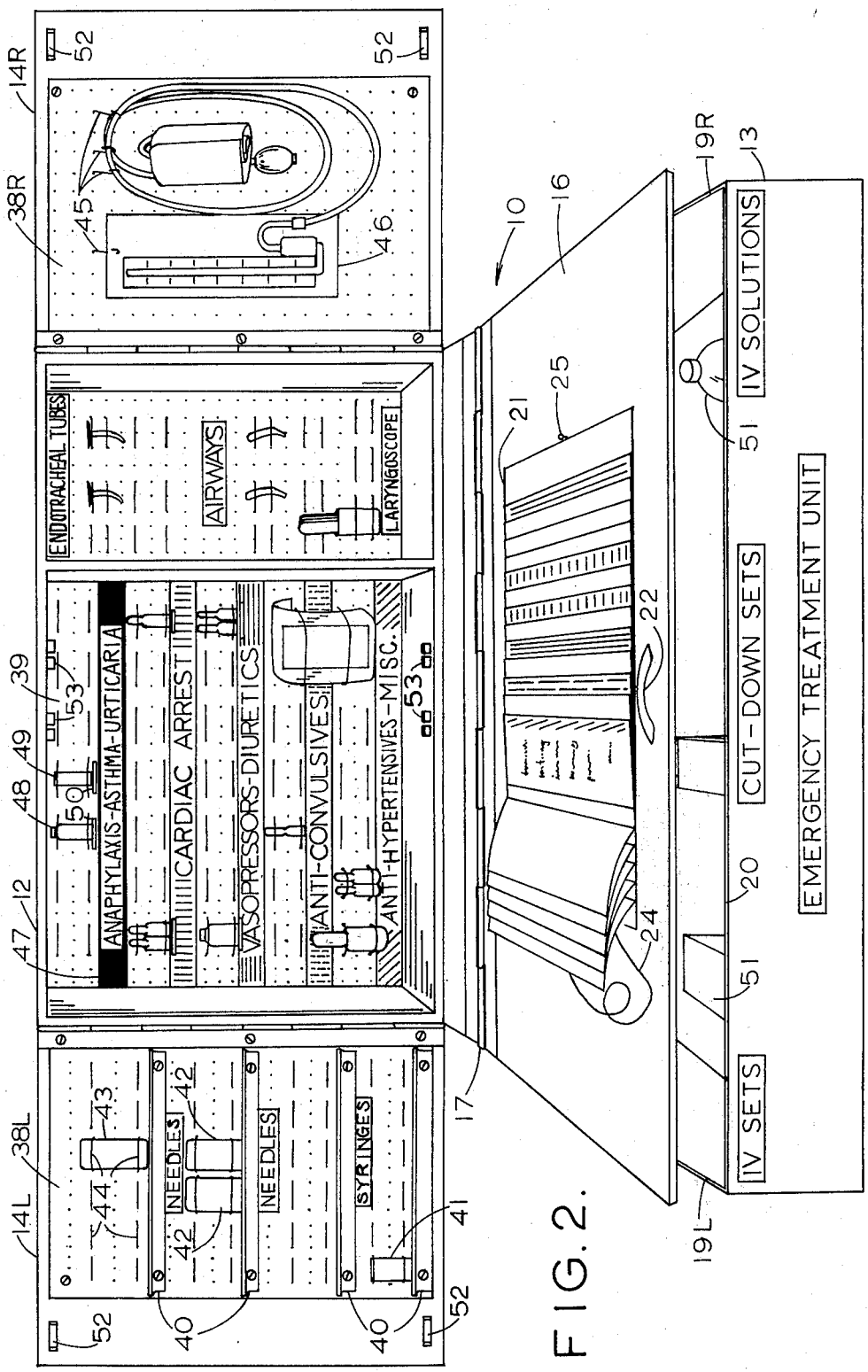

MEDICAL EMERGENCY TREATMENT CABINET

This invention relates in general to medical supply cabinets, and in particular, to a mobile medical emergency treatment cabinet that visibly displays and stores a variety of medications, supplies and equipment, color coded in convenient end use groups that are color keyed to equally convenient emergency treatment procedure instructions covering most common emergency situations encountered in hospital and clinic patient areas as well as other group assembly locations.

Most hospitals have special patient admitting rooms for emergency cases where the patient requires immediate attention to save his life, relieve his pain, or stabilize his physical condition. Such emergency rooms are usually equipped to handle any predictable emergency treatment requirement although the location and the accessability of medications, supplies and equipment within a given emergency room is often inadequate due to improper planning and insufficient procedures for maintaining assigned locations and quantities of such drugs, supplies and equipment. A shortage may arise when a particular piece of special equipment is borrowed for an emergency that arises in another area of the hospital facility. Any area of a hospital where patients are grouped such as patient admitting and discharging areas, operating and treatment rooms, wards, and examination areas is the potential location of an occurrence requiring emergency patient treatment. Other locations where such emergencies may occur exist in clinics, doctor and dentist offices, manufacturing plants, retail stores and restaurants, and public event facilities. Most of these locations, whether in a hospital or other place, have little or no provision for on the spot emergency treatment, particularly where cardiac arrest, hypertension, anaphylaxis, convulsions, acute asthmalaryngeal edema, urticaria, and the like are indicated. To receive proper emergency treatment the patient must usually be transported to a hospital emergency room, a procedure that can lose minutes or even hours of time critical to survival of the patient. Even when a rescue ambulance is summoned there is a loss of valuable time prior to initiation of emergency treatment.

Many prior developments in the field have amounted to no more than first aid cabinets stocked with bandages, antiseptics and patent medicines. Other medical service cabinets have been devices with inconvenient drawer storage, unorganized location of coordinate use items and a lack of mobility. Those units designed for serious medical emergencies are generally directed to treatment of a specific nature such as cardio-pulmonary resuscitation and are generally comprised of many pieces of expensive and technically complex equipment to provide rather complete treatment.

It is, therefore, a principal object of this invention to provide a mobile medical emergency treatment unit for hospitals, clinics, and other areas of potential use.

Another object of this invention is to provide such a unit with medications, supplies, and equipment conveniently grouped and displayed to facilitate use in emergency situations, to display supply depletion and to allow rapid inventorying of consumable items.

A further object with such a medical emergency treatment unit is to provide a system of color coded individual item location labels identifying coordinate use groups keyed to correspondingly color coded emergency instructions in an emergency treatment directions manual.

Still another object is to provide such a unit built from relatively inexpensive materials and stocked with medications, supplies, and equipment of standard commercial design and packaging.

A further object is to provide this unit with medications, supplies, equipment and instructions for optiminal use by paramedical personnel in emergency situations.

Features of this invention useful in accomplishing the above objects include, in a medical emergency patient treatment unit a cabinet design that minimizes hidden storage and maximizes visible display of color coded, coordinate end use grouped storage of medications, supplies and equipment. A set of instructions is included for specific emergency procedures useable by medical and paramedical personnel alike with a color code key system visibly coordinating specific procedure instructions with items useable in corresponding specific treatments.

A specific embodiment representing what is presently regarded as the best mode of carrying out the invention is illustrated in the accompanying drawings.

In the drawings:

FIG. 1 represents a perspective view of medical emergency treatment cabinet mounted on a standard wheeled base cabinet as it would appear when stationed on location available and ready for an emergency situation; and, FIG. 2, an enlarged front elevation view of the medical emergency treatment cabinet opened for emergency use and/or the taking of inventory.

Referring to the drawings:

The medical emergency treatment cabinet 10 of FIG. 1 is shown to be mounted on a lower fabricated base cabinet 11 that is of standard hospital bedside stand construction with light modifications for this useage. The medical emergency treatment cabinet 10 is divided into an upper cabinet section 12 and a lower storage bin 13. Two opposed left and right doors 14L and 14R that form the front of cabinet section 12 open and close on vertical left and right swing hinges 15L and 15R mounted on outer forward vertical edges of upper cabinet section 12 at the outer side edges of doors 14L and 14R. The lower storage bin 13 has an upward opening sloped full length lid 16 mounted on its rear edge by transversly extended pivot hinge 17 adjacent the lower forward edge of the upper fabricated cabinet section 12.

The side panels 18 of the medical emergency treatment cabinet 10 are so constructed that the lower storage bin lid 16 slopes forward and downward from its rear hinge 17 mounting to its front edge with the lid 16 resting on sloped side upper edges 19L and 19R and on the upper edge 20 of the front facing panel of storage bin 13. The sloped lid 16 forms a convenient mounting surface for emergency care instructions book 21 where the emergency care instructions are readily available for reference in emergency situations even though the lid is occasionally raised by raising the handle 22 to take something from storage bin 13. Instruction book 21 is held on the bin lid 18 by two fastener bolts 23 extended through the left binder edge of emergency care book instruction book 21 and through bin lid 16. An elastic band 24, fastened at opposite ends to the fastener bolts 23, is stretched over the care instruction book 21 and looped over a post bolt 25 also fastened to the bin lid 16 in a position adjacent to and just to the right of the instruction book 21. Thus, elastic band 24 firmly holds the instruction set pages and dividers closed in place when the care instruction book 21 is not in use. When an emergency situation arises the elastic band 24 is lifted off post bolt 25 with a flick of a finger and snaps out of the way due to its elasticity allowing the proper emergency care instruction set to be selected through a rapid color code index system described later.

The lower fabricated base cabinet 11 of standard construction is shown to have twin front opening doors 26L and 26R but may have a single front opening door (not shown) depending on the type of commercial cabinet selected. The lower base cabinet 11 is normally used for bulk storage of medications and supplies; particularly consumable items to back up the medications and supplies placed for rapid access (as described later) in the upper cabinet 12, and for storage of certain large pieces of emergency treatment equipment (not shown). The interior (not shown) of said lower cabinet 11 may be arranged with or without shelving depending on the particular mode of use contemplated. Descriptive legends 27 and 28 are mounted on the doors 26L and 26R to rapidly inform a user of the lower cabinet contents accessable through a particular door. The legends 27 and 28 are printed in large easily readable letters on appropriately colored background material to provide rapid identification. An over all unit identification and location legend 29 is also mounted prominently on the lower base cabinet 11. Castor wheels 30 at bottom corners of the lower base cabinet 11 facilitate mobility of the entire medical emergency patient treatment unit. Right angle type retainers 31 mounted on each upper corner of the lower base cabinet 11 help hold the medical emergency treatment cabinet 10 in place on top of lower base cabinet 11.

Referring again to the upper cabinet section 12 in FIG. 1, the doors 14L and 14R are shown to have quickly graspable handles 32 for quick opening when required. A red cross insignia 33 is shown on each door 14L and 14R for rapid identification that the unit 10 is of a medical nature and of course, other insignia or legends could be so provided as desired. A chest support board 34 is stored in a rectangular cross-section recess 35 inside the rear wall of and opening to one side of the upper fabricated cabinet 12. The lateral depth of the recess 35 is limited so that when the chest support board 34 is insertion stored a portion of the board 34 projects laterally to the side of the upper cabinet section 12. This is sufficient to provide visibility of the end of the board 34 including an identifying legend 36 thereon and to present ready accessability of the chest support board cut-out handle 37.

Referring also to FIG. 2, the inside surfaces of doors 14L and 14R and of the inside of the upper cabinet section 12 are shown to carry pegboard sheets 38L, 38R and 39 of rigid material having a plurality of regularly spaced through drilled holes useful for mounting various holding means. Door 14L also includes a plurality of shelves 40, made from linear pieces of rigid material having a generally "L" type cross-section, mounted on pegboard sheet 38L to the inside of door 14L to carry a plurality of containers such as the containers 41, 42, and 43. Elastic loops 44 of elastic band material laced through the holes of the pegboard 38L also help secure containers 41, 42, and 43 and other articles in place. Selected exposed elastic band material loops 44 are stretched around the containers 41, 42, and 43 and articles mounted on pegboard sheet 39 to hold them firmly in place but leaving them easily removable when needed. Items of lighter weight than those stored on pegboard 38L can be securely held by elastic loops 44 with no shelves being used on pegboard 39. Commercially available pegboard hangers 45 are used as the holding means on pegboard 38R for holding equipment items such as the sphygmomanometer 46 shown on pegboard 38R in a visible and accessable location.

Boldly printed legends on brightly colored materials color coded to identify groups of medications, supplies and equipment that may be used for treatment of specific emergencies are shown in FIG. 2 to be mounted on pegboard sheets 38L and 39. This color coding is consistent with color coding used on the emergency care instruction book 21 wherein instructions are arranged in groups of pages above divider pages, each of which has a brightly colored material backed legend mounted along the full length of its right edge. The colors used for the legends on the instruction set 21 key the instructions for a particular emergency treatment to groups and items of medications, supplies and equipment because each specific emergency situation, or group of situations where similar treatment is indicated, is assigned a specific color that is used throughout the medical emergency patient treatment unit 10.

With continued reference to FIG. 2, pegboard 39 carries legend 47 with the printed words "ANAPHYLAXIS- ASTHMA -URTICARIA" on a black background material. The small containers 48 and 49 contain medications or supplies used for the treatment of the named conditions which are grouped together because similar emergency treatment is indicated for any of these conditions. Individual containers 48 and 49 may be labeled with the names of the contents printed on black material to carry out the color code theme. Small individual container labels 50 are also mounted directly below containers 48 and 49 either above or on the upper portion of the general legend 47. Also any item located elsewhere within the entire medical emergency patient treatment unit 10 that is useable in treatment of the patient emergency situations named in the legend 47 generally is labeled in black. Where such item is also applicable to one or more patient emergency situations named under another code color, for example, pink for cardiac arrest or purple for convulsions, it will also be labeled in part with material of that color or colors. If a particular item or group is useable for any or all emergencies, for example, the intravenous supplies 51 in the lower storage bin 13 it is labeled with the common theme, red, of the overall unit 10 rather than with duplicate labels of all the code colors.

Continuing with the example under the code color black, when a doctor, nurse, or paramedical person is faced with an anaphylaxis emergency, a quick glance at the pegboard 39 and instruction book 21 references black as the code color for that particular emergency, the specific instructions are quickly found above the page divider labeled in black, and the medications, supplies, and equipment called for by the instructions are quickly located by the black legends and labels, or red if a general item is referenced. With all medications, supplies and equipment openly displayed and color coded, they are quickly obtained and put to use without the loss of time involved where drawer storage is used. Even bulky items stored in the lower storage bin 13 and lower base cabinet 11 are accessable with minimum time loss.

The upper cabinet section doors 14L and 14R are fitted with spring clamp type commercial cabinet interconnecting latches 52 and 53 of a conventional nature. This type latch holds the doors 14L and 14R securely closed yet releases said doors quickly when the door handles 32 are firmly pulled.

Whereas this invention is herein illustrated and described with respect to a specific embodiment hereof, it should be realized that various changes may be made without departing from essential contributions to the art made by the teachings hereof.

I claim:

1. In a medical emergency patient treatment unit, a cabinet structure with doors opening to display accessibly located medications, supplies, and equipment located in coordinate use groups; wherein such cabinet structure includes an upper section having said doors mounted by vertical hinges at the outer edges to close and open in and out from the mid-region, a bin below and extending forward from said upper section having the doors, a lid on the top of said bin, hinged at the rear adjacent the front of said upper section, with the bin lid and the top forepart of the bin sloping downwardly from the lid hinge to the front of the bin; emergency treatment instructions being fastened to the top of said bin lid, said instructions comprising color code indexed emergency treatment instruction sections respectively color coordinated with color coding of said coordinate use groups; a quick release elastic cord connected at opposite ends to emergency treatment instruction book bin lid fastening means, cord loop hook means fastened to said bin lid in position for book-page-hold-down by said elastic cord, when the cord is looped over said hook means; and bulk storage locations correspondingly color code labeled for special treatment equipment.

* * * * *